(12) United States Patent
Tretjak et al.

(10) Patent No.: US 12,122,746 B2
(45) Date of Patent: Oct. 22, 2024

(54) METHOD FOR MANUFACTURING HIGH-PURITY ALKYL ACRYLATES

(71) Applicant: Arkema France, Colombes (FR)

(72) Inventors: Serge Tretjak, Saint Avold (FR); Camille Hilpert, Saint Avold (FR)

(73) Assignee: Arkema France, Colombes (FR)

( * ) Notice: Subject to any disclaimer, the term of this patent is extended or adjusted under 35 U.S.C. 154(b) by 541 days.

(21) Appl. No.: 17/612,590

(22) PCT Filed: Apr. 23, 2020

(86) PCT No.: PCT/FR2020/050691
§ 371 (c)(1),
(2) Date: Nov. 19, 2021

(87) PCT Pub. No.: WO2020/234519
PCT Pub. Date: Nov. 26, 2020

(65) Prior Publication Data
US 2022/0234982 A1    Jul. 28, 2022

(30) Foreign Application Priority Data
May 23, 2019   (FR) ...................................... 1905414

(51) Int. Cl.
*C07C 67/54*   (2006.01)
*C07C 67/03*   (2006.01)
*C07C 67/08*   (2006.01)

(52) U.S. Cl.
CPC .............. *C07C 67/03* (2013.01); *C07C 67/08* (2013.01); *C07C 67/54* (2013.01)

(58) Field of Classification Search
CPC ......... C07C 67/03; C07C 67/08; C07C 67/54; C07C 69/54
See application file for complete search history.

(56) References Cited

U.S. PATENT DOCUMENTS

2013/0284586 A1* 10/2013 Lee ........................ B01D 3/141
                                                      203/99
2017/0267624 A1*  9/2017 Moreliere ............... C07C 67/08

FOREIGN PATENT DOCUMENTS

| EP | 2659943 A2 | 6/2013 |
|----|------------|--------|
| WO | WO16016528 A1 | 2/2016 |
| WO | WO18114429 A1 | 6/2018 |

* cited by examiner

*Primary Examiner* — Yate' K Cutliff
(74) *Attorney, Agent, or Firm* — Debodhonyaa Sengupta

(57) ABSTRACT

The invention relates to the manufacture of alkyl acrylates by direct esterification of acrylic acid by the corresponding alcohol. In particular, the invention relates to the use of a topping column equipped with a side draw-off making it possible to draw off a stream rich in acid impurities, such as β-hydroxypropionic acid and β-acryloyloxypropionic acid, during the distillation of the crude reaction mixture, in order to produce an acrylic ester meeting purity standards which are compatible with its use to prepare acrylic polymers.

10 Claims, 2 Drawing Sheets

[Fig. 1]
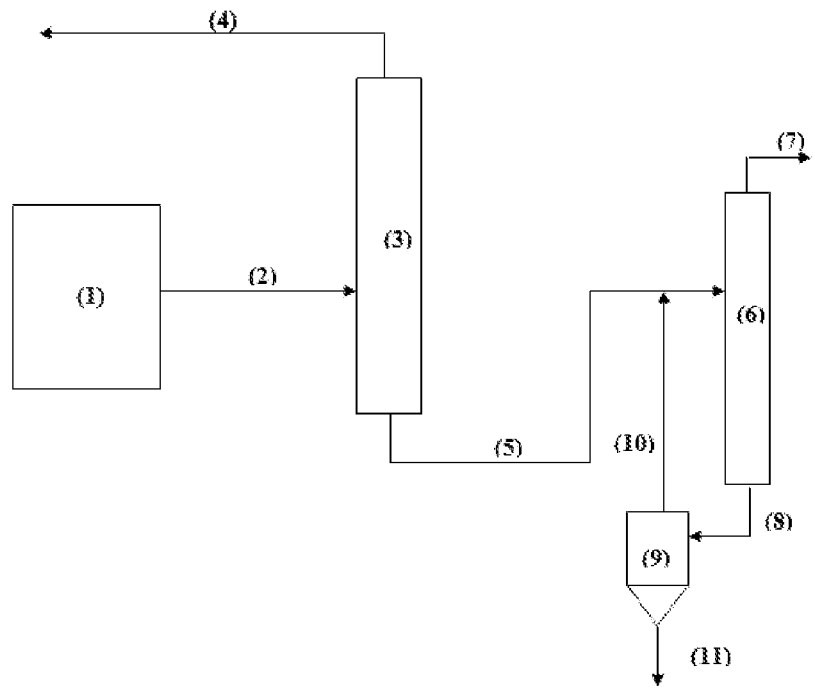
[Fig. 2]
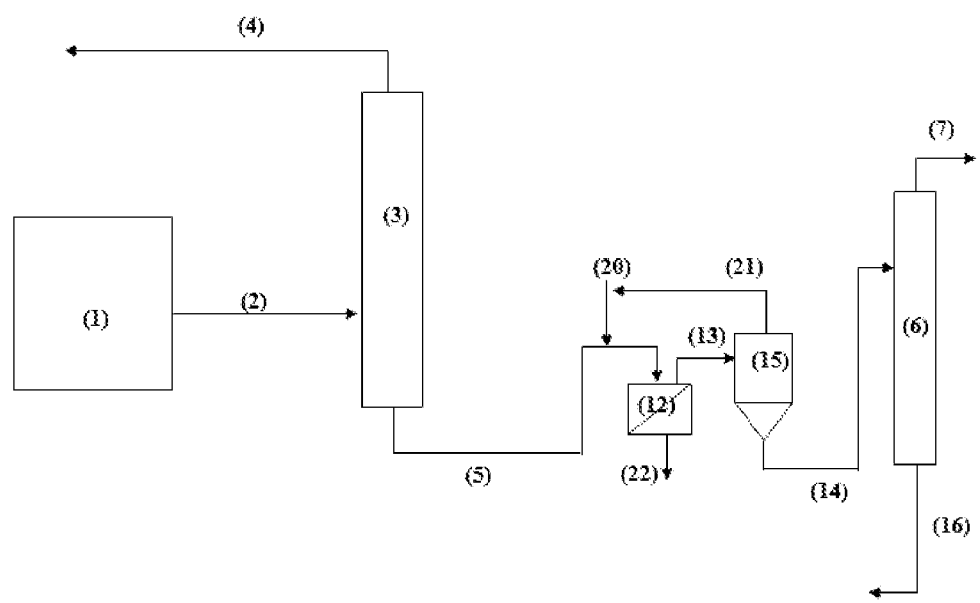

[Fig. 3]
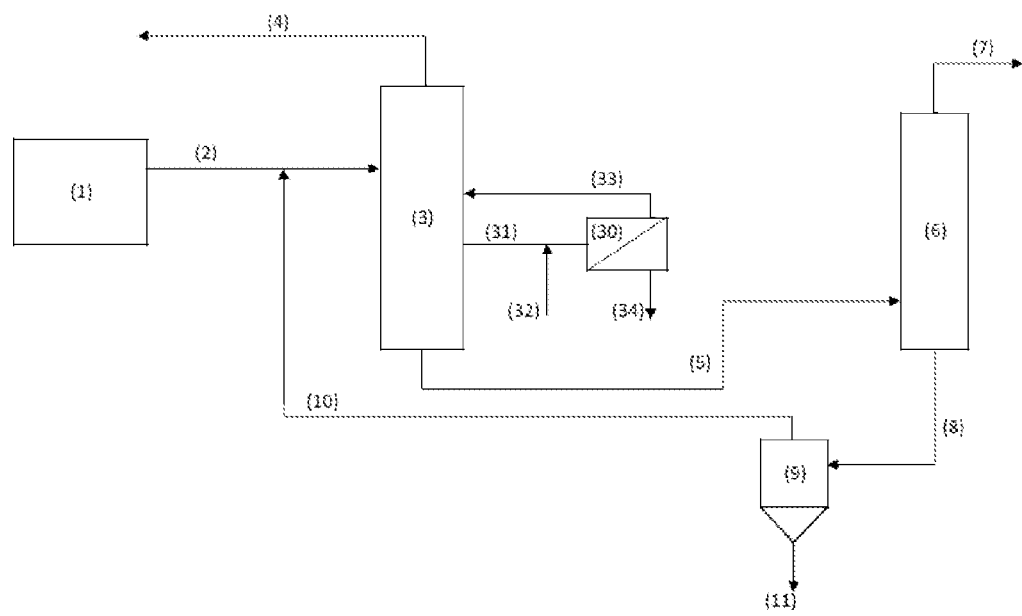

METHOD FOR MANUFACTURING HIGH-PURITY ALKYL ACRYLATES

CROSS-REFERENCE TO RELATED APPLICATIONS

This application is a national stage application under 35 U.S.C. § 371 of PCT/FR2020/050691, filed Apr. 23, 2020 which claims benefit to application FR19.05414, filed May 23, 2019.

TECHNICAL FIELD

The present invention relates to the manufacture of alkyl (meth)acrylates by direct esterification of (meth)acrylic acid by the corresponding alcohol.

A subject matter of the invention is a process for the purification of $C_4$-$C_{10}$ alkyl acrylate, in particular of 2-ethylhexyl acrylate, resulting in a high productivity of a product meeting the standards in terms of purity and of acidity, under optimized energy conditions.

TECHNICAL BACKGROUND AND TECHNICAL PROBLEM

The esterification of (meth)acrylic acid is an equilibrated reaction with generation of water, which it is necessary to remove during the reaction in order to shift the equilibrium in the direction of the production of the (meth)acrylic ester.

The problems that are posed during the manufacture of $C_4$-$C_{10}$ alkyl (meth)acrylates by direct esterification of (meth)acrylic acid, generally in the presence of a cationic resin as catalyst, are most often related to the complexity of the purification stages necessary after the reaction stage in order to obtain a product of high purity, generally to the detriment of the productivity of the process.

This is because the problem which is posed with the use of acrylic acid is that of the formation of β-hydroxypropionic acid (subsequently referred to as "HPA") and of β-acryloyloxypropionic acid (subsequently referred to as "AA dimer" or "di-AA").

HPA is probably formed from the AA dimer in the presence of water and on contact with the esterification catalyst. Its formation depends on the reaction operating conditions, on the nature of the catalyst used and on the amount of water present in the reaction medium. As regards the AA dimers, their formation is disadvantageous with regard to the amount of heavy byproducts to be separated and to be incinerated, and consequently disadvantageous for the productivity.

The same types of impurities can also be formed in the case of methacrylic acid, in particular β-hydroxymethylpropionic acid and β-methacryloyloxypropionic acid.

These byproducts present a problem of losses of starting materials and a problem of separation in order to be easily removed, all the more so as they can form azeotropes with the desired ester. It is therefore difficult to achieve a (meth) acrylic ester of high purity. In addition, the majority of the fields of application, in particular that of pressure-sensitive adhesives (PSAs), require the preparation of (meth)acrylic polymers from monomers meeting strict standards of purity (>99.7%) and devoid of acidity, in particular comprising a content of impurities related to the acid (HPA+di-AA or AA) of less than 90 ppm.

To solve these problems, the document WO 2016/016528 describes operating conditions making it possible to optimize the yield of the reaction and to effectively remove the water produced by the reaction, thus minimizing the side reactions responsible for the formation of acid impurities and heavy byproducts. These operating conditions are based on an excess of alcohol for the esterification reaction and the circulating of a reaction loop comprising only the esterification reactor and a distillation column which removes the water produced in the form of an azeotrope with the esterifying alcohol.

This process results in a purified ester containing low traces of impurities related to the acid. However, the solutions for reducing HPA in the event of drifts in the reaction (increase in the HPA content at the outlet of the reaction loop, for example following aging of the resin, a change in operating conditions or a reduced efficiency of the distillation column) are not envisaged. In particular, these drifts in the reaction can result, in the purification line, in a significant additional energy cost, and/or in the addition of a settling tank and of an evaporator having to treat the entire feed stream of the final purification column.

With the development of dividing wall distillation columns (known under the acronym DWC—dividing wall column), simplified purification processes are also proposed for producing (meth)acrylic esters of high purity.

The patent application EP 2 659 943 describes a configuration of a dividing wall column and its operation for producing a 2-ethylhexyl acrylate of high purity. Although this column is complex to manufacture and to operate, it exhibits the advantage of reducing the equipment cost and the energy consumption of the purification process, in comparison with a conventional plant comprising two distillation columns. The question of the stabilization necessary for the proper functioning of the dividing wall column and the problems associated with the separation of the HPA forming an azeotrope with the 2-ethylhexyl acrylate are not, however, solved.

In the document WO 2018/114429, a dividing wall column comprising a common lower portion connected to a single reboiler is used to purify 2-ethylhexyl acrylate or 2-propylheptyl acrylate. However, the issue of the formation of HPA is not addressed.

A need thus remains to improve the removal of acid impurities, in particular the removal of β-hydroxypropionic acid (HPA), in the processes for the synthesis/purification of acrylic esters described in the prior art.

It has now been discovered that the use of a distillation column equipped with a side draw-off and placed at the outlet of the reaction section makes it possible to continuously purge sideways a solution concentrated in HPA and acrylic acid dimers, and thus reduces the amount of residual acid impurities in the purified product. In addition, by combining the side draw-off with washing of the drawn-off solution with water, it is possible to recycle the acrylic ester present in the drawn-off phase, so as to minimize the losses of product.

A subject matter of the present invention is thus a process for the recovery/purification of alkyl acrylate which is simple to implement and which results in a product meeting the standards in terms of purity with an optimized productivity, while limiting the size of the items of equipment to be employed and the energy cost.

SUMMARY OF THE INVENTION

A subject matter of the invention is a process for the recovery/purification of a $C_4$-$C_{10}$ acrylic ester from a crude reaction mixture obtained by direct esterification of acrylic acid by the corresponding alcohol, characterized in that a stream rich in acid impurities, such as β-hydroxypropionic acid and β-acryloyloxypropionic acid, is drawn off via a side outlet during the distillation of the crude reaction mixture.

The term "stream rich in acid impurities" is understood to mean that the bulk of these acid impurities generated during the esterification reaction are present in the stream which is drawn off laterally from the distillation column fed with the crude reaction mixture.

This stream comprises, in addition to the acrylic ester, traces of unreacted reactants and heavy byproducts with a boiling point greater than that of the acrylic ester, and also traces of water.

The applicant company has surprisingly found that the profile of the distillation column used to remove the light compounds present in the crude reaction mixture (topping) exhibits a maximum concentration ("concentration bulge") for the acid impurities, which makes it possible to remove said impurities by side draw-off, using a distillation column equipped with a side draw-off.

The stream rich in acid impurities drawn off can be in gaseous form or in liquid form, preferably in liquid form.

The side draw-off is preferably carried out at a lower level than the level of feeding of the distillation column, which makes it possible to minimize the presence of the upgradable reactants, such as acrylic acid and the esterifying alcohol, in the drawn-off stream.

According to one embodiment of the process according to the invention, the stream rich in acid impurities, drawn off laterally, is subjected to a treatment with water, in order to separate said acid impurities and to recycle the treated stream in the distillation column.

According to one embodiment, the treated stream devoid of the bulk of the acid impurities is recycled in the distillation column.

The treated stream devoid of the bulk of the acid impurities can be recycled to the distillation column at a lower level or at a higher level than the side draw-off; preferably, it is recycled at a higher level than the side draw-off.

Preferably, the treated stream devoid of the bulk of the acid impurities is recycled to the distillation column at a lower level than the feed level of the distillation column.

The process according to the invention is carried out using a purification system comprising at least one distillation column equipped with a side draw-off making possible the separation of the bulk of the acid impurities present in the crude reaction mixture.

Preferably, said distillation column is a topping column separating the light compounds, such as the unreacted reactants present in the reaction medium, at the top.

Another subject matter of the invention is a process for the recovery/purification of a $C_4$-$C_{10}$ acrylic ester from a crude reaction mixture obtained by direct esterification of acrylic acid by the corresponding alcohol, comprising at least the following stages:
i) the reaction mixture is subjected to topping in a distillation column equipped with a side draw-off making it possible to obtain:
   at the top, a stream composed essentially of unreacted reactants;
   at the bottom, a stream comprising the desired ester and heavy byproducts;
   by side draw-off, a stream rich in acid impurities;
ii) the bottom stream from the topping column is subjected to a rectification column making it possible to separate:
   at the top, the purified desired ester,
   at the bottom, a stream containing heavy byproducts, which is concentrated on a film evaporator or distilled in a tailing column in order to recycle, to the topping column, the light compounds present and to remove a final residue of heavy byproducts.

The process according to the invention can additionally comprise a stage iii) of treatment of the stream drawn off laterally:
iii) the stream rich in acid impurities is subjected to a stage of washing with an aqueous stream making it possible to obtain, after separation by settling,
   an aqueous phase comprising all of the acid impurities, which can be sent to a biological treatment plant or in part used as aqueous washing stream, and
   an organic phase comprising the desired ester, heavy byproducts and traces of water and of reagents, which is recycled at least in part in the topping column.

The process according to the invention makes it possible to obtain a $C_4$-$C_{10}$ acrylic ester with a purity of greater than or equal to 99.7%, indeed even of greater than 99.8%, and comprising a content of acid impurities (HPA, AA dimer, AA) of less than 90 ppm, indeed even of less than 60 ppm.

In its preferred embodiment, additionally comprising the recycling after treatment of the stream drawn off laterally, the invention results in an optimized productivity while maintaining a reasonable energy balance.

The invention advantageously applies to the production of 2-ethylhexyl acrylate or of 2-octyl acrylate, meeting the purity standards required for the production of polymers which can be used, for example, in the field of adhesives or coatings.

Another subject matter of the invention is a process for the production of a $C_4$-$C_{10}$ acrylic ester devoid of acid impurities by direct esterification of acrylic acid by the corresponding alcohol comprising the recovery/purification process as defined above.

Other characteristics and advantages of the invention will emerge more clearly on reading the detailed description which follows, with reference to FIGS. 1, 2 and 3.

DESCRIPTION OF THE FIGURES

FIG. 1 represents a schematic diagram of a first purification process according to the prior art.

FIG. 2 represents a schematic diagram of a second purification process according to the prior art.

FIG. 3 represents a schematic diagram of the process according to the invention.

DETAILED DESCRIPTION OF THE INVENTION

The invention is based on the implementation of a purge of a stream rich in acid impurities using a side draw-off preferably equipping a topping column in a process for the purification of a crude reaction mixture obtained by direct esterification of acrylic acid by a $C_4$-$C_{10}$ alcohol.

The esterifying alcohol can be a primary or secondary aliphatic alcohol, comprising a linear or branched alkyl chain comprising from 4 to 10 carbon atoms. Mention may be made, as examples of alcohols, of butanol, 2-ethylhexanol, n-octanol, 2-octanol, n-decanol and 2-propylheptanol.

Preferably, the alcohol is 2-ethylhexanol or 2-octanol.

The esterification reaction is generally carried out in a reactor surmounted by a distillation column making it possible to extract the water generated by the reaction. The water of reaction is removed as it is formed in the form of an azeotrope with the esterifying alcohol in order to shift the esterification equilibrium.

The operating conditions of the esterification reaction are not critical, it being possible for the process according to the invention to be applied to the reaction mixture whatever the process for obtaining it. Thus, the reaction can be carried out in excess of acid or in excess of alcohol, at a temperature generally of between 70° C. and 100° C., preferably between 75° C. and 95° C.

The reactor can be a fixed bed reactor or a slurry bed reactor. The distillation column surmounting the reactor is generally a packed column and it is equipped with a top condenser and a settling tank, making it possible to separate by settling the vapors condensed at the top and to separate an organic phase comprising alcohol and traces of ester, which is recycled in the column, and an aqueous phase, which is removed. The column generally operates at a pressure ranging from 50 to 70 mmHg.

Use is generally made, as esterification catalyst, of a cationic resin, preferably a strong cationic resin, for example a strong cationic sulfonated resin of styrene/divinylbenzene type comprising sulfonic groups. Mention may be made, by way of example of resins, of those sold under the names Diaion® PK208 or PK216 by Mitsubishi, or those sold under the name Lewatit®K2620 or K2621 by Lanxess, or those sold under the name Amberlyst® A15, A16 or A46 by Rohm & Haas.

The esterification reaction is generally carried out in the presence of at least one polymerization inhibitor chosen from phenothiazine, hydroquinone (HQ) and its derivatives, such as hydroquinone methyl ether (HQME), 2,6-di(tert-butyl)-4-methylphenol (BHT), 2,4-dimethyl-6-(tert-butyl) phenol (Topanol A), salts of thiocarbamic or dithiocarbamic acid, N-oxyl compounds, such as 4-hydroxy-2,2,6,6-tetramethylpiperidinoxyl (4-OH-Tempo), compounds comprising nitroso groups, such as N-nitrosophenylhydroxylamine and its ammonium salts, quinones, such as benzoquinone, and amine compounds, such as para-phenylenediamine derivatives, at contents in the reaction medium which can be between 50 ppm and 5000 ppm, optionally in the presence of depleted air, but generally at contents of between 150 ppm and 1000 ppm. The addition of the polymerization inhibitors can be carried out at different places, with the introduction of the reactants or at the top of the distillation column.

With reference to FIG. 1, which represents the schematic diagram of a process for the recovery/purification of an acrylic ester according to the prior art, the crude reaction mixture (2) exiting the reaction zone (1) is sent to a topping column (3) which separates, at the top, a stream (4) comprising essentially the unreacted reactants and, at the bottom, a stream (5) comprising mainly the desired ester with impurities related to the acid and to the alcohol and heavy byproducts. The column (3) is, for example, a tray column, the trays being of perforated type, or a packed column. The stream (5) is sent to a rectification column (6) resulting, at the top, in a stream (7) of purified ester and, at the bottom, in a stream (8), which is concentrated on a film evaporator (9) or distilled in a topping column (not shown) in order to recycle the light compounds (10) present to the start of the purification section, such as traces of unreacted reactants, and to remove the final residue (11) of heavy products.

The stream (4) essentially comprises unreacted reactants, acrylic acid and esterifying alcohol, which are separated from the desired ester due to their lower boiling point. This upgradable stream (4) is recycled to the reaction.

According to this process of the prior art represented in FIG. 1, it is possible to adapt the operating conditions of the topping column (3) so as to entrain the HPA formed in the top stream recycled to the reaction. However, even if this embodiment makes it possible to limit the amount of acid impurities in the purified ester, it results either in an energy increase in the boiler of the topping column, if it is desired to keep the flow rate from the bottom to the column (6) for the purification of the ester constant, or in a drop in production by reducing the flow rate from the bottom of this topping column (3) to the purification column (6) for a constant energy cost.

With reference to FIG. 2, which represents the schematic diagram of a second process for the recovery/purification of an acrylic ester according to the prior art, washing the reaction mixture (2) with water after topping in the column (3) is carried out before separating the impurities and the heavy byproducts in the rectification column (6).

According to this embodiment, the bottom stream (5) from the topping column is subjected to washing with an aqueous stream (20) resulting, after separation by settling in a settling tank (12), in an aqueous phase (22) comprising all of the acid impurities and also in an organic phase (13) comprising the desired ester, heavy byproducts and traces of water and of acrylic acid.

The organic phase (13) obtained after washing with water is subjected to a stage of removal of water, by distillation using a distillation column or using a thin film evaporator (15), it being possible for the recovered water (21) to be recycled to the washing stage.

The water-free stream (14) is subsequently sent to the final column (6) for rectification of the pure ester, with removal at the bottom of a stream (16) of heavy byproducts.

Under these conditions, the distilled product (7) at the top of column (6) is a purified ester containing substantially no more acid impurities. However, in addition to the fact that a large-volume settling tank is required to treat the entire stream (5), it is necessary to treat a part of the washed stream by passing through an evaporator (15). This embodiment very greatly increases the energy consumption and is with difficulty compatible with a process on the industrial scale.

The invention overcomes the disadvantages of said processes of the prior art, by the use of a distillation column equipped with a side draw-off as topping column (3).

According to the schematic diagram of the process according to the invention, represented in FIG. 3, the reaction mixture (2) feeds a topping column comprising a side draw-off (3).

The internals used for the column (3) can be valve trays or perforated trays having a weir, or crosscurrent trays, such as dual flow trays, ripple trays or Shell Turbogrid trays, or stacked packing, such as structured packing, for example Mellapack 250X from Sulzer.

The topping column (3) advantageously comprises an equivalent of 10 to 30 theoretical stages, preferably of 15 to 20 theoretical stages.

The feeding of the topping column (3) by the stream (2) is generally carried out at the upper third of this column, preferably between the theoretical stages 3 to 10 counting from the top of the column.

The column operates with a reflux ratio (flow rate of condensed liquid returned to the column/flow rate (4) extracted at the top) advantageously of between 1/5 and 1/1, preferably of the order of 1/3.

The column (3) can operate under vacuum, in order to minimize the thermal exposure of heat-sensitive compounds within the column. Advantageously, the column (3) operates under a vacuum ranging from 1.333 to 13.332 kPa (10 to 100 mmHg).

The top stream (4) of the column (3) essentially comprises the unreacted reactants. This upgradable stream (4) is advantageously recycled to the reaction.

According to the invention, a stream (31) is drawn off laterally from the column (3). This stream (31) can be in gaseous form or in liquid form, preferably in liquid form. The draw-off is placed at a level lower than the feed level of the column, advantageously between the theoretical stages 5 to 15, preferably between 8 and 12, counting from the column top.

The location of this side draw-off is judiciously chosen so as to maximize the concentration of HPA and that of di-AA while minimizing the presence of upgradable reactants (acrylic acid and esterifying alcohol). This side draw-off generally comprises the amount of stabilizers necessary for its operation without fouling. If need be, in the event of gas-phase draw-off, another stabilizer can also be added. Advantageously, from 100 to 5000 ppm of polymerization inhibitor are introduced into the purification system according to the process of the invention. The polymerization inhibitors employed can be identical to those used to stabilize the esterification reaction.

According to one embodiment, the stabilization of the topping column (3) is carried out using a first polymerization inhibitor, preferably injected at the top condenser. The acrylic ester and also the IPA drawn off laterally from the column in the form of a gas stream or as a liquid stream can be stabilized with a different polymerization inhibitor from the first inhibitor. The organic stream (33) can also be stabilized with the first inhibitor before being reintroduced into the topping column.

In order to render the inhibitors more effective, oxygen, air or "depleted" air, comprising 7% $O_2$, can be injected at the bottom of the column (3). Preferably, the amount of oxygen injected corresponds to a content of 0.2% to 0.5/6, with respect to the amount of organic vapor in the column.

The drawn-off stream (31) is sent to a settling tank (30) to which water (32) is added. After cooling to a temperature preferably ranging from 20° C. to 70° C., water (32) is added in a proportion generally of between 5% and 50%, with respect to the stream (31) originating from the side draw-off.

After washing and separation by settling of the phases, the organic phase (33) is reintroduced into the column (3), at a level which can be lower or higher than that of the side draw-off, preferably at a higher level than that of the side draw-off, and preferably at a lower level than the feeding of the column, in particular between the theoretical stages 5 to 15, preferably 7 to 12. The aqueous phase (34) comprising the bulk of the acid impurities can be reused again to wash the stream (31) or sent for treatment to a biological plant.

The stream (5), separated at the bottom of the topping column (3), is sent to a rectification column (6) resulting, at the top, in a stream (7) of purified ester and, at the bottom, in a stream (8).

The column (6) is, for example, a perforated tray or packed column. The internals used for the column can be valve trays or perforated trays having a weir, or crosscurrent trays, such as dual flow trays, ripple trays or Shell Turbogrid trays, or stacked packing, such as structured packing, for example Mellapack 250X from Sulzer.

The distillation column (6) advantageously comprises an equivalent of 2 to 15 theoretical stages, preferably of 5 to 10 theoretical stages.

The column (6) operates with a reflux ratio (flow rate of condensed liquid returned to the column/flow rate of the stream (7)) ranging from 1/5 to 1/1, preferably of the order of 1/2.

The column (6) can operate under vacuum, in order to minimize the thermal exposure of heat-sensitive compounds within the column. Advantageously, the column (6) operates under a vacuum ranging from 1.333 to 13.332 kPa (10 to 100 mmHg).

Advantageously, its operating temperature is between 50° C. and 160° C.

The stream (8) separated at the bottom is concentrated on a thin film evaporator (9) in order to recycle the light compounds present to the start of the purification section upstream of the column (3) or of the column (6) and makes it possible to remove the residue (11) comprising the heavy products.

According to the invention, the top stream (7) of the column (6) consists of the desired ester having, as specifications, an ester purity of greater than 99.7% and a content of acid impurities (HPA+diAA+AA) of less than 90 ppm. The water content is generally less than 400 ppm.

The examples below illustrate the present invention without, however, limiting the scope thereof.

EXPERIMENTAL PART

In the examples, the percentages are shown by weight, unless otherwise indicated, and the following abbreviations were used:
AA: acrylic acid
2EHA: 2-ethylhexyl acrylate
2EH: 2-ethylhexanol
HPA: β-hydroxypropionic acid
Di-AA: AA dimers
PTZ: phenothiazine In the experimental part, with reference to FIGS. 1 and 2 according to the prior art and to FIG. 3 according to the invention, the columns 3 and 6 have a fixed configuration.

The main characteristics of these two columns are as follows:
Column 3: 45 trays of dual flow type (counting from the column top)
  Column top pressure: 25 mmHg
  Feeding: tray 15
  Air: tray 45
  PTZ stabilizer: tray 1
Column 6: 25 trays of dual flow type (counting from the column top)
  Column top pressure: 20 mmHg
  Feeding: tray 25
  Air: tray 25
  PTZ stabilizer: tray 1

Example 1 (Reference)

The feed stream 2 of a topping column (3) of a process for the purification of 2-ethylhexyl acrylate represented in FIG. 1 contains 75 ppm of HPA in a first trial and 140 ppm of HPA in a second trial.

The conditions for implementing the process and the composition of the various streams are summarized in table 1 below.

Under the conditions of the trial 1, where the HPA content in the feed stream of the purification line is 75 ppm, the installation represented in FIG. 1 makes it possible to manufacture 4950 kg/h, i.e. approximately 119 t/d, of 2EHA with a purity of 99.7% and comprising acid compounds (di-AA+AA 4 HPA) at a content of 84 ppm. This product meets commercial specifications.

The energy involved in this trial in the boiler of columns 3 and 6 and in the evaporator 9 is 2 222 618 kcal/h.

Under the conditions of the trial 2, where the HPA content in the feed stream of the purification line is 140 ppm, for an energy involved in the boiler of the columns 3 and 6 and in the evaporator 9 which is substantially equivalent (2 222 813 kcal/h), the installation represented in FIG. 1 does not make it possible to manufacture a 2EHA meeting the specifications relating to the content of acid compounds (<90 ppm), the overall content of Di-AA+AA+HPA in the stream 7 being 156 ppm, and the purity of the 2EHA of 99.6% is outside the specification.

TABLE 1

|  |  | Stream | | | | |
| --- | --- | --- | --- | --- | --- | --- |
|  |  | 2 | 4 | 5 | 7 | 11 |
| Trial 1 | Temperature, ° C. | 115 | 29.7 | 143.1 | 23.8 | 138 |
|  | Flow rate by weight, kg/hr | 13 600 | 7570.199 | 6300 | 4949.999 | 331.745 |
|  | Fraction by weight |  |  |  |  |  |
|  | AA | 0.065 | 0.119 | 0 | 0 | 0 |
|  | 2EH | 0.231 | 0.423 | 0 | 0 | 0 |
|  | 2EHA | 0.649 | 0.405 | 0.941 | 0.997 | 0.326 |
|  | WATER | 0.005 | 0.008 | 0 | 0 | 0 |

TABLE 1-continued

|  | Stream | | | | |
| --- | --- | --- | --- | --- | --- |
|  | 2 | 4 | 5 | 7 | 11 |
| Di-AA | 0.001 | 10 | 0.002 | 29 | 0.007 |
| HPA, ppm | 142 | 170 | 108 | 127 | 35 |

Example 2 (Comparative)

The trial 2 of example 1 is reproduced while changing certain operating conditions in order to find a product meeting the specifications.

Thus, in the trial 3, the flow rate by weight of the stream 4 distilled at the top of the topping column 3 is increased, with the consequence of a drop in the flow rate for the production of 2EHA (stream 7 at the top of the column 6).

In the trial 4, the reboiling flow rate of the topping column 3 is increased, with the consequence of an increase in the energy consumption of the purification process.

The results are collated in table 2.

The conditions of the trial 3 result in a product meeting the specifications, with a slightly lower energy consumption (2 209 593 kcal/h) than the trial 1. However, a loss in productivity is observed (107 t/d instead of 119 t/d).

The conditions of the trial 4 generate a 2EHA in accordance with the specifications and for a productivity equivalent to that of the trial 1, but with an overconsumption of energy of the order of 10%.

TABLE 2

|  |  | Stream | | | | | |
| --- | --- | --- | --- | --- | --- | --- | --- |
|  |  | 2 | 4 | 5 | 7 | 11 | 8 |
| Trial 3 | Temperature, ° C. | 115 | 29.7 | 143.1 | 23.8 | 138 | 144.3 |
|  | Flow rate by weight, kg/hr | 13 600 | 8070.384 | 5800 | 4449.998 | 331.723 |  |
|  | Fraction by weight |  |  |  |  |  |  |
|  | AA | 0.065 | 0.111 | 0 | 0 | 0 |  |
|  | 2EH | 0.231 | 0.396 | 0 | 0 | 0 |  |
|  | 2EHA | 0.649 | 0.442 | 0.937 | 0.998 | 0.326 |  |
|  | WATER | 0.005 | 0.008 | 0 | 0 | 0 |  |
|  | Di-AA | 0.001 | 11 | 0.002 | 22 ppm | 0.007 |  |
|  | HPA, ppm | 140 | 211 | 41 | 50 | 13 |  |
| Trial 4 | Flow rate by weight, kg/hr | 13 600 | 7570.203 | 6300 | 4949.999 | 331.963 | 1350 |
|  | Fraction by weight |  |  |  |  |  |  |
|  | AA | 0.065 | 0.119 | 0 | 0 | 0 | 0 |
|  | 2EH | 0.231 | 0.423 | 0 | 0 | 0 | 0 |
|  | 2EHA | 0.649 | 0.405 | 0.942 | 0.998 | 0.326 | 0.735 |
|  | WATER | 0.005 | 0.008 | 0 | 0 | 0 | 0 |
|  | Di-AA | 0.001 | 9 | 0.002 | 29 | 0.007 | 0.007 |
|  | HPA, ppm | 140 | 220 | 44 | 52 | 14 | 15 |

TABLE 1-continued

|  |  | Stream | | | | |
| --- | --- | --- | --- | --- | --- | --- |
|  |  | 2 | 4 | 5 | 7 | 11 |
|  | Di-AA | 0.001 | 10 ppm | 0.002 | 29 ppm | 0.007 |
|  | HPA, ppm | 75 | 99 | 47 | 55 | 15 |
| Trial 2 | AA | 0.065 | 0.119 | 0 | 0 | 0 |
|  | 2EH | 0.231 | 0.423 | 0 | 0 | 0 |
|  | 2EHA | 0.649 | 0.406 | 0.94 | 0.996 | 0.325 |
|  | WATER | 0.005 | 0.008 | 0 | 0 | 0 |

Example 3 (Comparative)

With reference to FIG. 2, the bottom stream 5 from the topping column 3 is sent to a settling tank 12 and is washed with 20% of water at 70° C. The organic stream 13 is taken up by a film evaporator 15 before being subjected to distillation in the column 6: the aqueous stream 22 is sent to biological treatment and the top stream 21 from the evaporator is sent back to the feed of the settling tank 12.

The compositions of the different streams are summarized in table 3.

TABLE 3

| | Stream | | | | | | | | |
|---|---|---|---|---|---|---|---|---|---|
| | 2 | 4 | 5 | 20 | 22 | 14 | 21 | 16 | 7 |
| Temperature, ° C. | 115 | 29.7 | 143 | 20 | 20 | 110 | 110 | 138 | 23.8 |
| Flow rate by weight, kg/hr | 13600 | 7570.284 | 6300 | 1260 | 1471.025 | 6317.276 | 432.724 | 17.03 | 4967.236 |
| Cumulative flow rate by vol./hr | 16.88 | 8.627 | 7.991 | 1.262 | 1.499 | 7.777 | 2389.327 | 0.017 | 5.631 |
| Fraction by weight | | | | | | | | | |
| AA | 0.063 | 0.116 | 0 | 0 | 0 | 0 | 0 | 0 | 0 |
| 2EH | 0.225 | 0.412 | 0 | 01 | 0 | 0 | 0 | 0 | 0 |
| 2EHA | 0.658 | 0.42 | 0.943 | 0 | 0 | 0.976 | 0.963 | 0.316 | 0.996 |
| WATER | 0.005 | 0.008 | 0 | 1 | 0.856 | 0 | 0.031 | 0 | 0 |
| Di-AA, ppm | 181 | 3 | 395 | 0 | 10 | 0 | 0 | 0 | 0 |
| HPA, ppm | 136 | 186 | 75 | 0 | 315 | 0 | 0 | 0 | 0 |

The overall treatment of the stream 5 makes it possible to reduce to 0 ppm the content of acid compounds in the stream feeding the column 6. This results, at the column top, in a distilled stream 7 devoid of acid compounds. However, the 99.6% purity of the distilled 2EHA does not meet the specification in terms of purity.

Furthermore, the energy cost of this operation is 18% greater than that required for a process without intermediate washing.

Example 4 (According to the Invention)

Example 1 is reproduced (trial 2) but in a configuration according to the invention (represented in FIG. 3). The feed stream (2) contains 140 ppm of HPA.

The stream 31 is drawn off at the tray 26 of the column 3 and washed in a settling tank 30 with water 32. The organic phase 33 is recycled at the tray 22 of the column 3 and the aqueous phase 34 is sent to biological treatment. The separation by settling in the settling tank 30 is carried out with 20% of water, with respect to the stream 31, at a temperature of 70° C.

It is found that the treatment of the stream 31 drawn off laterally makes it possible to reduce the content of acids (HPA+Di-AA) to 58 ppm while keeping to the overall specification for 2EHA at 99.7% for the stream 7 extracted at the top of column 6 (see table 4).

Furthermore, the energy cost of this operation is only 1% greater than the cost of the implementation of comparative example 1, for a production increased to 124 t/d.

Example 5 (According to the Invention)

Example 4 is reproduced while changing certain operating conditions, with a production of 2EHA maintained at 119 t/d and the HPA content in the feed stream 2 set at 140 ppm.

Effect of the Separation by Settling Temperature of the Settling Tank 30

The separation by settling temperature in a range from 20° C. to 70° C. has no influence on the performance qualities of this treatment (table 5).

TABLE 5

| Separation by settling T° (° C.) | 20 | 50 | 70 |
|---|---|---|---|
| Flow rate of the stream 31 (kg/h) | 300 | 300 | 300 |
| Flow rate of the stream 32 (kg/h) | 60 | 60 | 60 |
| Production of the stream 7 (t/d) | 119 | 119 | 119 |
| Energy employed (kcal/h) | 2 239 082 | 2 235 646 | 2 233 537 |
| Stream 7 (fraction by weight) | | | |
| AA, ppm | 0 | 0 | 0 |
| 2EHA, % | 99.7 | 99.7 | 99.7 |
| Di-AA, ppm | 28 | 28 | 28 |
| HPA, ppm | 56 | 57 | 57 |

Effect of the Flow Rate for Side Draw-Off of the Stream 31

The increase in the flow rate of the side draw-off 31 makes it possible to improve the acidity content in the purified stream 7 without, however, increasing the level of purity maintained at 99.7% (table 6).

TABLE 4

| | Stream | | | | | | | | |
|---|---|---|---|---|---|---|---|---|---|
| | 2 | 4 | 5 | 7 | 8 | 11 | 31 | 33 | 34 |
| Temperature, ° C. | 115 | 29.7 | 143.1 | 23.8 | 144.2 | 138 | 138.9 | 70 | 70 |
| Flow rate by weight, kg/hr | 13600 | 7365.358 | 6500 | 5149.999 | 1350 | 319.548 | 1000 | 995.525 | 204.475 |
| Fraction by weight | | | | | | | | | |
| AA | 0.065 | 0.122 | 0 | 0 | 0 | 0 | 0 | 0 | 0 |
| 2EH | 0.23 | 0.434 | 0 | 0 | 0 | 0 | 0.002 | 0.002 | 0 |
| 2EHA | 0.649 | 0.389 | 0.943 | 0.997 | 0.74 | 0.326 | 0.95 | 0.954 | 0.001 |
| WATER | 0.005 | 0.009 | 0 | 0 | 0 | 0 | 0 | 0.005 | 0.953 |
| Di-AA | 0.001 | 0 | 0.001 | 29 | 0.007 | 0.006 | 0 | 0 | 0.001 |
| HPA, ppm | 140 | 44 | 25 | 29 | 9 | 8 | 2000 | 62 | 0.007 |

TABLE 6

| Separation by settling T° (° C.) | 20 | 20 | 20 |
|---|---|---|---|
| Flow rate of the stream 31 (kg/h) | 300 | 1000 | 10 000 |
| Flow rate of the stream 32 (kg/h) | 60 | 200 | 60 |
| Production of the stream 7 (t/d) | 119 | 119 | 124 |
| Energy employed (kcal/h) | 2 239 082 | 2 258 023 | 2 263 410 |
| Stream 7 (fraction by weight) | | | |
| 2EHA | 99.7 | 99.7 | 99.7 |
| AA, ppm | 0 | 0 | 0 |
| Di-AA, ppm | 28 | 29 | 29 |
| HPA, ppm | 56 | 25 | 26 |

Effect of the Amount of Washing Water 32 Introduced into the Stream 31

The flow rate of washing water, with respect to the flow rate of the stream drawn-off laterally, has little influence on the washing treatment (table 7).

TABLE 7

| Separation by settling T° (° C.) | 70 | 70 |
|---|---|---|
| Flow rate of the stream 31 (kg/h) | 300 | 300 |
| Flow rate of the stream 32 (kg/h) | 30 | 60 |
| Production of the stream 7 (t/d) | 119 | 119 |
| Energy employed (kcal/h) | 2 235 646 | 2 233 537 |
| Stream 7 (fraction by weight) | | |
| 2EHA | 99.7 | 99.7 |
| AA, ppm | 0 | 0 |
| Di-AA, ppm | 28 | 28 |
| HPA, ppm | 59 | 57 |

The invention claimed is:

1. A process for the recovery/purification of a $C_4$-$C_{10}$ acrylic ester from a crude reaction mixture obtained by direct esterification of acrylic acid by the corresponding alcohol, comprising the step of drawing off a stream rich in acid impurities as a side draw-off via a side outlet of a distillation column during distillation of the crude reaction mixture.

2. The process as claimed in claim 1, wherein the stream rich in acid impurities is drawn off in gaseous form or in liquid form.

3. The process as claimed in claim 1 wherein the side draw-off is carried out at a first location on the distillation column, the crude reaction mixture is fed to the distillation column at a second location on the distillation column, and the first location is at a lower height than the second location.

4. The process as claimed in claim 1 wherein the side draw-off is treated with water to produce a treated stream, and the treated stream is recycled to the distillation column.

5. The process as claimed in claim 4, wherein the treated stream is recycled to the distillation column at a third location on the distillation column, the side draw-off is carried out at a first location on the distillation column, and the third location is at a higher height than the first location.

6. The process as claimed in claim 4 wherein the crude reaction mixture is fed to the distillation column at a second location on the distillation column, and the third location is at a lower height than the second location.

7. A process for the recovery/purification of a $C_4$-$C_{10}$ acrylic ester, from a crude reaction mixture obtained by direct esterification of acrylic acid by the corresponding alcohol, comprising at least the following stages:
   i) subjecting the reaction mixture to topping in a topping column equipped with a side draw-off, a topping column top outlet and a topping column bottom outlet to obtain:
      at the topping column top outlet, a topping column top stream consisting essentially of unreacted reactants;
      at the topping column bottom outlet, a topping column bottom stream comprising desired ester and heavy byproducts;
      at the side draw-off, a side stream rich in acid impurities;
   ii) feeding the bottom stream from the topping column to a rectification column equipped with a rectification column top outlet and a rectification column bottom outlet to separate:
      at the rectification column top outlet, purified desired ester;
      at the rectification column bottom outlet, a rectification column bottom stream containing heavy byproducts, which is concentrated on a film evaporator or distilled in a tailing column in order to recycle, to the topping column, the light compounds present and to remove a final residue of heavy byproducts.

8. The process as claimed in claim 7, additionally comprising a stage iii) of treating the side stream rich in acid impurities:
   iii) subjecting the side stream rich in acid impurities to a washing stage with an aqueous stream to obtain, after separation by settling,
      an aqueous phase comprising all of the acid impurities, and
      an organic phase comprising the desired ester, heavy byproducts and traces of water and of reagents, which is recycled at least in part in the topping column.

9. The process as claimed in claim 1 wherein the acrylic ester is 2-ethylhexyl acrylate.

10. A process for the production of a $C_4$-$C_{10}$ acrylic ester devoid of acid impurities by direct esterification of acrylic acid by the corresponding alcohol comprising the recovery/purification process as defined according to claim 1.

* * * * *